United States Patent
Rebmann

(10) Patent No.: US 8,652,494 B2
(45) Date of Patent: Feb. 18, 2014

(54) COMPOSITION FOR COSMETIC, PHARMACEUTICAL OR DIETARY APPLICATIONS

(75) Inventor: Herbert Rebmann, Neustadt (DE)

(73) Assignee: Lipoid GmbH, Ludwigshafen (DE)

( * ) Notice: Subject to any disclaimer, the term of this patent is extended or adjusted under 35 U.S.C. 154(b) by 0 days.

(21) Appl. No.: 13/405,028

(22) Filed: Feb. 24, 2012

(65) Prior Publication Data

US 2012/0156272 A1 Jun. 21, 2012

Related U.S. Application Data

(63) Continuation of application No. PCT/IB2009/052707, filed on Jun. 24, 2009.

(51) Int. Cl.
- *A61K 8/02* (2006.01)
- *A61K 9/00* (2006.01)
- *A01N 65/00* (2009.01)
- *A61K 36/00* (2006.01)

(52) U.S. Cl.
USPC ............ 424/401; 424/400; 424/725

(58) Field of Classification Search
USPC .......................................... 424/400
See application file for complete search history.

(56) References Cited

U.S. PATENT DOCUMENTS

| | | | |
|---|---|---|---|
| 4,229,360 A | 10/1980 | Schneider et al. | |
| 5,470,581 A * | 11/1995 | Grillo et al. | 424/479 |
| 5,635,491 A | 6/1997 | Seki et al. | |
| 5,783,211 A | 7/1998 | Manzo et al. | |
| 5,800,818 A * | 9/1998 | Prugnaud et al. | 424/744 |
| 5,843,347 A * | 12/1998 | Nguyen et al. | 264/9 |
| 6,221,385 B1 | 4/2001 | Camu et al. | |
| 6,387,398 B1 | 5/2002 | Vollhardt et al. | |
| 6,399,094 B1 | 6/2002 | Brandl et al. | |
| 2003/0099674 A1* | 5/2003 | Chen | 424/400 |
| 2005/0181054 A1* | 8/2005 | Nishibe et al. | 424/473 |
| 2005/0226942 A1* | 10/2005 | Myhill et al. | 424/725 |
| 2006/0013779 A1 | 1/2006 | Dodds et al. | |
| 2007/0212407 A1* | 9/2007 | Jacquet | 424/451 |
| 2008/0261916 A1 | 10/2008 | Jaszberenyi et al. | |
| 2010/0055051 A1* | 3/2010 | Dougherty et al. | 424/48 |
| 2010/0062067 A1* | 3/2010 | Tonge et al. | 424/489 |

FOREIGN PATENT DOCUMENTS

| | | |
|---|---|---|
| DE | 1 813 390 | 7/1970 |
| EP | 0 209 037 | 1/1987 |
| EP | 0 599 543 | 6/1994 |
| WO | 84/01689 | 5/1984 |
| WO | 86/03938 | 7/1986 |
| WO | WO 2008065451 A2 * | 6/2008 |
| WO | WO 2008078212 A1 * | 7/2008 |

OTHER PUBLICATIONS

International Search Report dated Jul. 27, 2010 in Application No. PCTIB2009/052707.

* cited by examiner

*Primary Examiner* — Robert T Crow
*Assistant Examiner* — Doan Phan
(74) *Attorney, Agent, or Firm* — Staas & Halsey LLP

(57) ABSTRACT

A composition including 0.5-40% vegetable extracts, 30-90% carbohydrate and 0.5-30% of phospholipid with 40-80% phosphatidylcholine for cosmetic, pharmaceutical or dietary uses.

10 Claims, No Drawings

COMPOSITION FOR COSMETIC, PHARMACEUTICAL OR DIETARY APPLICATIONS

This application is a continuation application filed under 35 U.S.C. §111(a) of International Application No. PCT/IB2009/052707, filed Jun. 24, 2009, the entire contents of which are incorporated herein by reference.

FIELD OF THE INVENTION

The present invention is related to a composition comprising vegetable essence and/or ingredients and/or active agents, carbohydrate and phospholipid, a method for production of such a composition and the pharmaceutical, dietary or cosmetic application of such a composition.

BACKGROUND OF THE INVENTION

Vegetable resources are of continuously increasing importance for the preparation of pharmaceutical, dietary or cosmetic applications. The demand for purely natural models is of increasing importance. Vegetable resources, particularly vegetable essences with active agents are not always stable and in most of the cases difficult to insert into a model.

The document U.S. Pat. No. 5,387,415 discloses the production of *Aloe vera* juice pellets by seeping said juice with with collagens into liquid azote at −196° C. The method is very onerous at high energy consumption. A similar method is taught in U.S. Pat. No. 5,401,502.

The document U.S. Pat. No. 5,387,415 discloses bisabolol nanoparticles, pre-emulsion with lecithin in a high pressure homogenizer, subsequently spray dried by means of starch and maltodextrin. It has always to be worked with a starch dye. The products are spray dried. Many vegetable extracts and their ingredients are very sensitive and may be decomposed or exhausted during spray drying. Said decomposition or exhaustion ought to be avoided.

The document U.S. Pat. No. 5,180,713 discloses the production of pharmaceutical liposomes in organic solvents in the presence of cryoprotectants, such as sugar. It has to be worked in organic solvents, being difficult to remove from the end-product and being unwanted in natural products.

The document U.S. Pat. No. 6,534,087 discloses foamed pills of active agents; lecithin and maltodextrin. Measured powders or granules with stable characteristics can't be produced like that.

The document US 20040234673 discloses a composition with an amorphous carbohydrate phase, a crystalline phase and a third phase, selected from one or more substances made of aroma, volatile substances and substances sensitive towards external impacts, the third phase being dispersed by means of emulsifiers in the other two phases. Any extrusion of this composition is carried out at high temperatures. By working at higher temperatures the ingredients of the vegetable extracts are decomposed and their intended activity can not be provided.

The patent applications EP 209037, EP 209038, EP 275005, EP 275224, EP 283713, EP 300282, EP 304603, EP 441279, EP 464297, EP 1390008, EP 1837030, EP 1844785 disclose stabilization of vegetable extracts by complex formation of the active agents with phospholipids. For this work has to be done in solvents, such as methylene chloride or methanol. This mode of operation is very elaborate and requests the use of questionable solvents.

The problems of formulation and the limited stability during transport and storage of the compositions of the state of the art are due to the selection of their components, particularly the quality of the lecithins with shares of phosphatidylcholine of less than 15%.

SUMMARY OF THE INVENTION

The object of the present invention is therefore to provide a composition with a high share of vegetable extracts and/or ingredients and/or active agents, with a high stability during transport and storage and easily and gently to work to formulations. It is a further object of the invention to provide a method for the production of such a composition and suitable applications for such a composition.

The inventive compositions contain 0.5-40% of vegetable extract and/or vegetable active agents, 10-90% of a carbohydrate and 0.5-30% of a phospholipid. Preferred are compositions with 18-35% of vegetable extract and/or vegetable active agents, 40-80% carbohydrate and 1-25% phospholipids. Particularly preferred are compositions with 30% of vegetable extract and/or vegetable active agents, 67% carbohydrate and 3% phospholipids. The compositions allow high shares of active agents in the formulations. The compositions are free of conservation-means and solvents and consist mostly of natural vegetable resources.

Vegetable resources may be extracts from plants or parts of plants, fruit concentrates, herbs extracts, vegetable oils and alike, such as Acai-extract (*Euterpe oleracea*), Acerola extract (*Malpighia glabra*), Field Horsetail (*Equisetum arvense*), Agarius extract (*Agarius blazei* murill), Aloe (*Aloe vera, Aloe Barbadensis*), Apple extract (*Malus*), Artichoke leave extract (*Cynara scolymus*), Artichoke flower extract (*Cynara edulis*), Arnica (*Arnica Montana*), oysters extract, *Ostrea edulis*), valerian root extract (*Valeriana officinalis*), bearberry leave extract (*Artostaphylos uva-ursi*), bamboo extract (*Bambus vulgaris*, Bamboo), Bitter melon extract (*Momordica charantia*), Bitter orange extract (*Citrus aurantium*), Nettle leave extract (*Urtica dioica*), Nettle-root-extract (*Urtica dioica*), Broccoli extract (*Brassica oleracea*), Water cress (*Rorippa nasturtium*), Painted Nettle extract (*Coleus forskohlii*), Capsicum extract (*Capsicum frutescens*), Centella asiatica (Gotu Kola), Cinchona extract (*Cinchona*), Cranberry extract (*Vaccinium vitis-daea*), Curcuma extract (*Curcuma longa*), Damiana extract (*Tunera diffusa*), Red Pitaya extract (*Pitahaya*), Echinacea Purpurea, wheaten Placenta extract, Edelweiss extract (*Leotopodium alpinum*), Ivy extract (*Hedera helix*), Earth-root-spine extract (*Tribulus terrestris*), Garcinia Cambogia extract (*Garcinia Cambogia*), Ginkgo extract (*Ginkgo biloba*), Ginseng extract (*Panax ginseng*), Pomegranate extract (*Punica granatum*), Grapefruit extract (*Citrus paradisi*), Griffonia extract (*Griffonia simplicifolia*), Green tea extract (*Camellia sinensis*), Guarana extract (*Paullinia cupana*), cucumber extract (*Cucumis sativus*), Rose hip extract (*Rosa canina*), Blueberry extract (*Vaccinium myrtillus*), Hibiskus extract (Malvacea, Malvenextrakt), Honey extracts, Hop extract (*Humulus*), Ginger extract (*Zingiber officinale*), Iceland Moss (*Ceteraria islandica*), Jojoba extract (*Simmondsia chinensis*), St. Johns Wort, (*Hypericum Perforatum*), Coffee concentrate, Cacaobeans extract (*Theobroma cacao*), Cactusflower extract, Chamomile flower extract (*Matricaria recutita*, Chamomile, *Matricaria Chamomila*), Carrot extract (*Daucus carota*), Kiwi extract (Aperygidae), Kudzu extract (*Pueraria lobata*), Coconut milk extract, Pumpkin seed extract (*Curcubita pepo*), Cornflower extract (*Centaurea cyanus*), Lotus extract, Dandelion root extract (*Taraxacum officinale*), Maca extract (*Lepidium peruvianum*), Magnolia flower extract, Mango extracts, Holy thistle extract (*Silybum marianum*), Marie gold (*Calendula Officiennalis*), Mate extract (*Ilex paraguariensis*), Butcher's broom extract (*Rugcus aculeatus*), Sea alga extracts, Cranberry, (Kraanbeere, *Vaccinium macrocarpon*), Moringa Oleiferaextrakt, Musk Mallow (*Malva moschata*), Evening primrose oil extract (*Azadirachta indica*), Nettle extract (Urticaceae), Olive leave extract (*Olea europea*), Orange extract (Hespridin), Orchide extract, *Papaya* extract (*Carica papaya*), Peppermint extracts, *Carica papaya* (*Geissospermum*), Sour Orange extract (*Citrus aurantioum*), Cowberry extract (*Vaccinium vitas-ideea*), Pygeum Afrikanum extract (*Prunus africana*), Herbasec extracts, Resveratrol extract (*Polygonum cuspidatum*), Rooibos (*Aspalasthus Linnearis*), Rose hip extract, Horse chestnut extract (*Aesculus hippocastanum*), Rosmary, (*Rosemarinus Officinalis*), Red clover extract (*Trifolium platense*), Red wine extract (*Vitis vinifera*), Saw Palmetto extract (*Serenoa repens*), Salade extract (*Lactuca sativa*), Sandal-wood extract (*Santalum rubrum*), Sage, (*Salvia Officinalis*), Horsetail extract (*Equisetum*), Milfoil (*Achillea millefolium*), Black Pepper extract (*Piper nigrum*), Black tea extract, Water lily extract (*Nymphaea*), White Willow, (Willow Bark, *Salix Alba*), Licorize (*Glycyrrhiza*), Rampion root extract (*Harpagophytum procumbens*), Thyme extract (*Thymus vulgaris*), Tomato extract (*Lycopersicum esculentum*), Grapeseed extract (*Vitis vinifera*), Grape peel extract (*Vitis vinifera*), *Rorippa amphibia*, Willow bark-extract (*Salix alba*), Incense extract (*Artemisia absinthium*), White tea extract, Yam extract (*Dioscorea opposita*), Yohimbin extract (*Pausinystalia yohimbe*), Witch hazel (*Hamamelis*), Cinnamon extract (*Cinnamomum cassia* Presl), Lemon extract (*Citrus*), Onion extract (*Allium cepa*).

Vegetable active agents or ingredients may be used apart from the extracts alone or in combination. Vegetable active agents may be: *glycyrrhizin*, coffein, proanthocianidin, hesperitin, rutin, luteolin, polyphenols, aspalatin, oleuropin, theobromin, bioflavanoids or combinations of *glycyrrhizin* and *Glycerica glabra* extracts, coffein und *Camellia sinesis* or *Camellia alba* or *Guarana* (*Paulinia cubana*) or *Coffes arabica*, proanthocianidin and *Vitis vinifera* (Vine), hespiridin and rutin und *Citrus aurantii* amara peel extract, luteolin and *Chamomilla reticulataq*, polyphenols and *Camellia sinensis* or *Vaccinium macrocarpon* (Cranberry), coffein/theobromin and *Ilex paraguaiensis* (Mate), bioflavanoids and Green tea extract (*Camellia sinensis*), Curcumin and *Curcuma longa*, epigallocatechingallate, catechin, epicatechine, narginin, hesperidin, neohesperidin, asiaticiside, ellagitannin, chlorogen acid, oleuropei, arbutin, betuli, esculin, sylimarin, etc., particularly isoflavone puerin (from or with *Pueraria lobata* extract), oleuropein (from or with *Olea europea* Leaf extrakt), luteolin (from or with *Chamilla reticulate*), Baicalin (from or with *Scutellaria balcalinensis* Rott extract), Chorogenic acid (from or with *Eucommia ulmoides*/Guttapercha tree extract), apigenin (from or with *Citrus grandis* peel extract), hesperidin (from or with *Citrus aurantium* amara peel extract), coffein (from or with *Paulinia cubana*/Guarana extract), aspalatin (from or with *Aspalatus linnearis*/Rooibos extract), rutin (from or with *Sophora japonica* extract), polyphenol, quinic acid (from or with *Vaccinium marcrocarpon*/Cranberry extract), allagitannins (from or with *Punica granatum*/Pomegranate extract), Asiaticoside (from or with *Centella asiatica* extract), proanthocianidine (from or with *Vitis vinifera* extract (Proanthocianidine), rutin (from or with *Viola odorata* extrakt), 18 beta Glycyrrhetic acid (from or with *Liquiritia* extract), Glycyrrhizin (from or with *Liquiritia* extract), theanin, polaphenols (from or with *Camellia/Thea sinsnesis* extract), coffeolychinic acid, caffeine, theobromone (from or with *Ilex paraguaiensis*/Mate extract).

Phospholipids may be phospholipids and phospholipid-fractions of vegetable resources, such as from soya beans, Sunflowers, Rape, peanut, corn, Lupines or cotton seed or egg yolk phospholipids with a share of phosphatidylcholine of 20-100%. Or defined phospholipids such as Di-acyl-phosphatidylcholine (e. g. Dimyristoyl-, Dipalmitoyl-, Disteraoyl-phosphatidylcholine), hydrated phospholipids, hydrolized or modified phospholipids. Phospholipid-fractions are preferred with a share of phosphatidylcholin of 40-80%.

Lecithin is composed of neutralipids, glycolipids and phospholipids. The Phospholipids are composed of e. g. phosphatidylcholine (PC), phosphatidylethanolamin (PE), phosphatidylinositol (PI), phosphatidylserin (PS), lysophosphatidylcholine (LPC), lysophosphatidylethanolamine (LPE), lysophosophatidylinositol (LPI) usw. (A. Wendel Lecithin, Kirk-Othmer Encyclopedia of Chemical Technology, Fourth Edition, Volume 15; Willem van Nieuwenhuyzen, Fett/Lipid 99 (1997, Nr. 1, S10-14, Willem van Nieuwenhuyzen, Eur. J. Lipid Sci. Technol 2008, 110, 472-486. Customary lecithin contains about. 12-15% phosphatidylcholine. De-oiled lecithin, as well called pure lecithin, contains 20-25% phosphatidylcholine. Phospholipid-fractions with shares of 30 to 100% phosphatidylcholine may be produced by fractioning with ethanol. Customary products enriched with phosphatidylcholine are e.g. phospholipids of soy as e.g. Lipoid S 20 (approx. 20-24% PC, 16-22% PE), Lipoid S45 (45% PC, 10-18% PE), Lipoid S75 (70% PC, 7-10% PE), Lipoid S80 (75% PC, 7% PE), Lipoid S100 (>94% PC), phospholipon 20 (about 20-24% PC, 16-22% PE), phospholipon 50 (approx. 45-50% PC), phospholipon 85G (>80% PC), phospholipon 90G (>95% PC) or phospholipids of rape, such as e. g. Lipoid R20 (approx. 20-24% PC, 16-22% PE), Lipoid R75 (70% PC, 7-10% PE), Lipoid R45 (45% PC, 10-18% PE), Lipoid R75 (75% PC, 7% PE), Lipoid R80 (75% PC, 7% PE), Lipoid R100 (>94% PC) or soy phospholipids from genetically non modified (non GMO) soy beans such as e. g. Lipoid P45 (45% PC, 10-18% PE), Lipoid P75 (75% PC, 7% PE) , Lipoid P100 (>94% PC).

Sugar (mono-, di-, or polysaccharides) like manit (mannitol), glucose (dextrose), trehalose (mykose), saccharose (sucrose), lactose (milk sugar), fructose (levulose), mannose, ribose, galactose, fructose, rhamnose, lactulose, maltose, raffinose, dextrin or maltodextrin are used for carbohydrates. Mannit, glucose, trehalose are preferred and particularly preferred is maltodextrin.

The inventive composition is produced by dissolving or dispersing the elements simultaneously or subsequently at room temperature in water and by homogenizing in customary devices, such as for example by a microfluidizer, 1-3 cycles, after that filtration or sterile filtration, e.g. by a 2-8 µm filter-candle and subsequently by freeze- or vacuum-drying gently at −30° C. to +45° C. The dried product may be ground to the wanted grain size in suitable devices with an orifice diameter of 0.5-1.5 mm.

Liposomal compounds may be produced at redispersing.

The dried composition is stable for transport and storage and easy to work into cosmetic, dietary and pharmaceutical formulations. Advantages are the good solubility, the wettability of the active agent is improved, the characteristics at dispersion of the active agents are optimized, the stability of the active agent against environmental impacts is improved, odor and taste of the active agent is optimized.

During treatment of the new composition in cosmetic, dietary and pharmaceutical formulations the best bio-disposability is achieved.

Formulations are e. g. oral, such as powders, granules, pills, capsules and topic preparations such as creams, lotions, etc. by adding the customary additives.

EXAMPLES

Example 1

*Aloe Vera* 10 kg (10%) is mixed with 87 Kg (87%) maltodextrin and 3 kg (3%) Lipoid P45 and dispersed in 100 kg water and subsequently 2× homogenized by means of a microfluidizer. The dispersion is then sterile filtered above a 0.2 µm filter candle at laminar flow, frozen at −30° C. and dried in vacuum at −35° C. till max. +45° C. The agglomerates are ground after drying.

Example 2

White tea extract: 30%
Maltodextrin: 67%
Lipoid P45: 3%
The production corresponds to example 1.

Example 3

Green tea extract: 30%
Maltodextrin: 67%
Lipoid P45: 3%.
The production corresponds to example 1.

Example 4

Hibiscus extract: 30%
Maltodextrin: 67%
Lipoid P 45: 3%.
The production corresponds to example 1.

Example 5

Guarana extract: 30%
Maltodextrin: 67%
Lipoid P 45: 3%
The production corresponds to example 1.

Example 6

Lemon acid: 15%
Vine acid: 10%
Milk acid: 5%
Aerosil: 5%
Maltodextrin: 62%
Lipoid P45: 3%
The production corresponds to example 1.

Example 7

White tea extract: 20%
Maltodextrin: 70%
Lipoid S20: 10%
The production corresponds to example 1.

Example 8

Green tea extract (with 1% caffeine and 5% polyphenols) 40%
Threhalose 59%
Lipoid S75 1%.
The production corresponds to example 1.

Example 9

Guarana extract 20%
Glucose 78%
Phospholipon 80.2%.
The production corresponds to example 1.

Example 10

White tea extract 28%
Mannit 70%
Lipoid S80 2%
The production corresponds to example 1. Cosmetic preparations are preferred.

Example 11

Production of a Soft Cream
Phase A: 40.0 g SLM 2005 (SLM 2005=Lipoid SLM 2005=base formulation consisting of hydrated soy lecithin, ethanol, glycerin and middle chain triglycerides).
Phase B: 82.8 g distilled water, 0.2 g Keltrol CGG-SFT (xanthan rubber product with laminar-fluid rheology for transparent solvents, particularly conceived for use as cosmetic and further products for body care. Dust free thin fluid powder stable over a large pH array), 1.0 g phospholipon 80H, 1.0 g composition according example 1-5.
Phase C: 36.0 g miglyol, 12.0 g Jojoba oil, 2.0 g Vitamin E-acetate.
Phase D: 12.0 g ethanol, 6.0 g glycerin, 6.0 g hydrolite, 1.0 g panthenol.
The Phase B is heated up to 60-65° C. till all elements are solved and subsequently worked into phase A while stirring at 40° C., after that stirred in phase C and after that phase D is added while stirring ca. 1 min. at Ultra-Turax at 40° C. homogenized.

Example 12

Production of a Soft Cream
Phase A: 40.0 g SLM 2005
Phase B: 77.8 g distilled water, 0.2 g keltrol CG-SFT, Phospholipon 80H
Phase C: 36.0 g miglyol, 12.0 g, Jojoba oil, 2.0 g tocopherolacetat
Phase D: 12.0 g ethanol, 6.0 g glycerin, 6.0 g hydrolyte, 1 g pathenol
Phase E: 5.0 g distilled water, 1.0 g of the composition according to example 1-5.
The phase B is heated up till 60-65° C. till all components are dissolved and subsequently while stirring at 40° C. worked in to phase A, then phase C is added while stirring and homogenized. After that at 40° C. homogenized phase D is added and while stirring ca. 1 min. at Ultra-Turax at 40° C. homogenized.
After that phase E is added while cold stirring.

Example 13

Production of a Lotion
Phase A: 20.0 g SLM 2005
Phase B: 107.6 g distilled water, 0.4 g keltrol CGG-SFT=xanthan Gum (s. o.), 3.0 g, phospholipon 80H, 1.0 g. Composition according example 1-5, 1.0 g panthenol.
Phase C: 30.0 g miglyol, 6.0 g Jojoba oil, 2.0 g tocopherolacetate
Phase D: 14.0 g ethanol, 106.0 g glycerin, 6.0 g hydrolyte The phase B is heated up till 60-65° C. till all components are dissolved and subsequently while stirring at 40° C. worked in to phase A, then phase C is added and stirred homogenous. After that phase D is added and while stirring ca. 1 min. at an Ultra-Turax at 40° C. homogenized.

Example 14

Production of a Lotion
Phase A: 20.0 g SLM 2005
Phase B: 97.6 g distilled water, 0.4 g keltrol CGG-SFT, 3.0 g phospholipon 80H=hydrated phospholipid with ca. 80% phosphatidylcholine, 1.0 g composition according example 1-5, 1.0 g panthenol.
Phase C: 30.0 g miglyol=fatty acid ester, 6.0 g Jojoba oil, 1.0 g tocopherolacetat, 14.0 g ethanol, 10.0 g glycerin, 6.0 g hydrolite.
Phase D: 10.0 g distilled water, 1.0 g of the composition according example 1-5.

The phase B is heated up till 60-65° C. till all components are dissolved and subsequently while stirring at 40° C. worked in to phase A, then phase C is added and stirred homogenous. After that phase D is added and while stirring ca. 1 min. at an Ultra-Turax at 40° C. homogenized.

Example 15

Cream
Phase A: 18.0 g miglyol 812, 9.0 g tegosoft DC, 10.0 g Avocado oil, 6.0 g lanette 18, 2.0 g Tegin M, 0.2 g stearin acid, 1.0 g tocopherolacetat
Phase B: 2.0 g tegoCare Cg 90; 6.0 g glycerin, 1.0 g panthenol, 0.4 g allatoin, 132.2 g water.
Phase C: 1.0 g of the composition according example 1-5, 9.0 g water
Phase D: 0.4 g preserving agent.

The phases A and B are respectively heated up till 80 C. Phase B is worked into phase A while stirring and subsequently post-homogenized 1 min. by an Ultra-Turax.

What is claimed is:

1. A composition consisting of:
   a) 0.5-40 weight % vegetable extract;
   b) 30-90 weight % maltodextrin; and
   c) 0.5-30 weight % phospholipid including 40-80% of phosphatidylcholine.
2. The composition according to claim 1, consisting of:
   a) 18-35 weight % of the vegetable extract;
   b) 40-80 weight % of the maltodextrin; and
   c) 1-25 weight % of the phospholipid.
3. The composition according to claim 1, consisting of:
   a) 28-32 weight % of the vegetable extract;
   b) 60-70 weight % of the maltodextrin; and
   c) 2-8 weight % of the phospholipid.
4. The composition according to claim 1, consisting of:
   a) 30 weight % of the vegetable extract;
   b) 67 weight % of the maltodextrin; and
   c) 3 weight % of the phospholipid.
5. The composition according to claim 1, wherein the composition is provided in a dry form as a powder or as granules.
6. The composition according to claim 5, wherein the dry form is a lyophilisate.
7. The composition according to claim 6, wherein the composition spontaneously forms liposomes when redispersing.
8. The composition according to claim 1, wherein the vegetable extract is selected from the group consisting of *Aloe*, Rooibos, Guarana, white tea, green tea, black tea, Hibiskus, Nettle, Rofippa amphibia, water cress, horse tail, field horsetail, chamomile, *Centella asiatica, Gingko, Ginseng*, Cranberry, olive, pomegranate or mixtures thereof.
9. A method for the production of a composition according to claim 1, wherein the vegetable extract, the maltodextrin and the phospholipid are dispersed and homogenized in water, then sterile filtered and subsequently dried at −30° C. to +45° C., and the dried product is ground to a grain size with an orifice diameter of 0.5-1.5 mm.
10. The composition according to claim 1 as a cosmetic, dietary or pharmaceutical formulation.

* * * * *